US006486334B1

(12) United States Patent
Yu et al.

(10) Patent No.: US 6,486,334 B1
(45) Date of Patent: Nov. 26, 2002

(54) BIOMEMBRANE MIMETIC SURFACE COATINGS

(75) Inventors: Hyuk Yu, Blue Mounds, WI (US); Charles M. Strother, Madison, WI (US); Xiqun Jiang, Madison, WI (US); Sangwook Park, Taejon (KR)

(73) Assignee: Wisconsin Alumni Research Foundation, Madison, WI (US)

( * ) Notice: Subject to any disclaimer, the term of this patent is extended or adjusted under 35 U.S.C. 154(b) by 16 days.

(21) Appl. No.: 09/891,083

(22) Filed: Jun. 25, 2001

(51) Int. Cl.$^7$ ............... C07F 1/12; C07F 9/02; C07F 1/10
(52) U.S. Cl. ............ 554/74; 554/81; 554/82; 556/24; 556/113
(58) Field of Search ............ 554/74, 81, 82; 556/24, 113

(56) References Cited

U.S. PATENT DOCUMENTS

| 5,380,589 A | 1/1995 | Goodman et al. ........ 428/36.92 |
| 5,801,260 A | * 9/1998 | Yu et al. ................ 554/81 |

OTHER PUBLICATIONS

Z. Yang et al., Protein Interactions With Poly(ethylene glycol) Self–Assembled Monolayers On Glass Substrates, Diffusion And Adsorption; 15 Langmuir 8405–8411 (1999).

Z. Yang et al., Preserving A Globular Protein Shape On Glass Slides: A Self–Assembled Monolayer Approach, 9 Adv. Mater. 426–429 (1997).

Z. Yang et al., Biomembrane Mimetic Surfaces By Phospholipid Self–Assembled Monolayers On Silica Substrates, 15 Langmuir 1731–1737 (1999).

C. Pidgeon et al., Immobilized Artificial Membrane Chromatography: Supports Composed of Membrane Lipids, 176 Anal. Biochem. 36–47 (1989).

R. Nuzzo et al., 105 J. Am. Chem. Soc. Adsorption Of Bifunctional Organic Disulfides On Gold Surfaces, 4481–4483 (1983).

T. Li et al., Intramolecular Electron Transfer At Metal Surfaces . . . 106 J. Am. Chem. Soc. 6107–6108 (1984).

K. Prime et al., Self–Assembled Organic Monolayers: Model Systems For Studying Adsorption Of Proteins At Surfaces 252 Science 1164–1167 (1991).

D. Seebach et al., β–Peptides . . . 79 Helv. Chim. Acta 913–941 (1996).

M. Bodanszky et al., The Practice Of Peptide Synthesis, 119 Springer–Verlag, Berlin (1984).

\* cited by examiner

*Primary Examiner*—Porfirio Nazario-Gonzalez
(74) *Attorney, Agent, or Firm*—Quarles & Brady LLP

(57) ABSTRACT

Disclosed are thiol-functionalized phospholipids that have been covalently linked to a gold and/or silver substrate, methods for making them, and intermediates useful for such purposes. The resulting material creates a biomimetic surface that can be included in a conduit containing blood.

8 Claims, 2 Drawing Sheets

BIOMEMBRANE MIMETIC SURFACE COATINGS

CROSS REFERENCES TO RELATED APPLICATIONS

Not applicable.

STATEMENT REGARDING FEDERALLY SPONSORED RESEARCH

This invention was made with United States government support awarded by the following agencies: NSF DMR-9711226. The United States has certain rights in this invention.

BACKGROUND OF THE INVENTION

The present invention relates to artificial biocompatible surfaces. More particularly it relates to surfaces which mimic monolayer phospholipid structures in humans.

A wide variety of medical devices have been developed for insertion into the human body to form part of the human blood circulation system (e.g. vascular grafts; heart valves), and/or to be positioned at locations exposed to human blood (conduits in heart lung machines). However, clots, clogs and other problems can develop if such surfaces are not specially designed to minimize such problems (e.g. by making them biomimetic). In some applications this can even lead to increased risk of stroke.

Biomimetic surfaces are also of interest in connection with protein chromatography, biological sample support, enzyme immobilization, and DNA surface computing. They are also of interest for researching biological mechanisms.

Some artificial conduits have been produced that have surfaces that are formed by taking mold impressions from naturally occurring surface via microcasting. See e.g. U.S. Pat. No. 5,380,589. The disclosure of this patent, and of all other publications referred to herein, are incorporated by reference as if fully set forth herein. However, this molding technique is somewhat costly, and is not suitable for certain applications.

It has also been proposed to graft biocompatible polymer chains onto a substrate using a silicon linkage to form a biocompatible surface. See Z. Yang et al., 15 Langmuir 8405–8411 (1999) and Z. Yang et al., 9 Adv. Mater. 426–429 (1997). However, this approach is unlikely to be useful in certain in vivo applications requiring long-term stability and durability.

There has also been some discussion of covalently linking phospholipids on a silicate gel surface for chromatography applications. See C. Pidgeon et al., 176 Anal. Biochem. 36 (1989).

In Z. Yang et al., 15 Langmuir 1731–1737 (1999) it was proposed to form biomembrane mimetic surfaces by phospholipid self-assembled monolayers. However, the linkage we proposed relied on silicon. This rendered the structure unsuitable for certain in vivo applications.

There has also been discussion of the use of thiol linkages between some compounds and fixed surfaces. See e.g. R. Nuzzo et al., 105 J. Am. Chem. Soc. 4481 (1983); T. Li et al., 106 J. Am. Chem. Soc. 6107 (1984); and K. Prime et al., 252 Science 1164 (1991). However, in each case the compounds did not sufficiently address biomimetic needs.

Thus, a need exists for biomimetic surfaces which are compatible with the human body, stable long-term, and durable.

BRIEF SUMMARY OF THE INVENTION

One aspect the invention provides a compound having the following moiety:

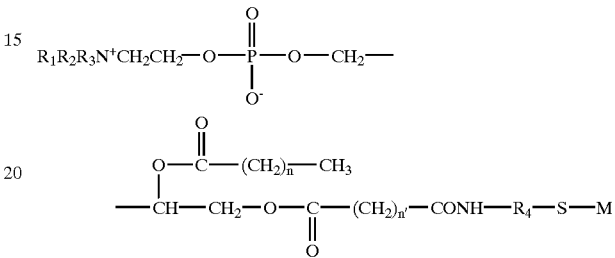

wherein $R_1$, $R_2$ and $R_3$ are individually selected from the group consisting of $CH_3$ and H, n is 10 to 24, $R_4$ is alkyl with less than six carbons, n' is 10 to 24, and M is selected from the group consisting of Au, Ag and mixtures thereof. In a preferred form both n and n' are 12, M is Au, each of $R_1$, $R_2$ and $R_3$ are $CH_3$, and $R_4$ is $CH_2CH_2$.

In another aspect, the invention provides a method of forming such compounds. One reacts a compound having the following moiety:

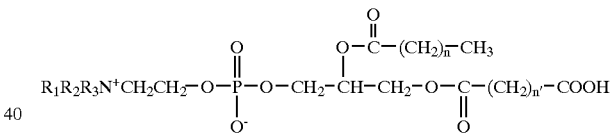

with $H_2N$—$R_4$—SH, and then covalently links the resultant to M. $R_1$, $R_2$ and $R_3$ are individually selected from the group consisting of $CH_3$ and H, $R_4$ is alkyl with less than six carbons, n is 10 to 24, n' is 10 to 24, and M is selected from the group consisting of Au, Ag and mixtures thereof.

Still another aspect the invention provides a compound having the following formula:

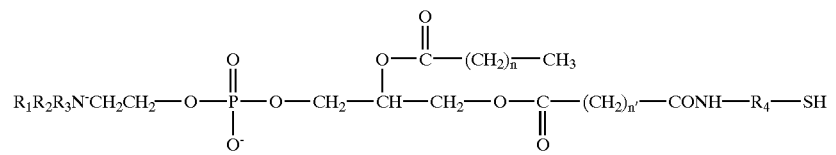

wherein $R_1$, $R_2$ and $R_3$ are individually selected from the group consisting of $CH_3$ and H, $R_4$ is alkyl with less than six carbons, n is 10 to 24, and n' is 10 to 24. In a preferred form both n and n' are 12, each of $R_1$, $R_2$ and $R_3$ are $CH_3$, and $R_4$ is $CH_2CH_2$.

There is a naturally occurring phospholipid in many blood-containing conduits. We have developed a way to stably link this type of phospholipid to a durable substrate (e.g. gold coated glass). The resulting array presents a well ordered monolayer of exposed phospholipid that closely mimics a layer of the naturally occurring material.

Advantages of the present invention are to provide biomimetic surfaces that can be efficiently produced and which appear to be highly compatible with the human body. Further, such structures appear to be highly durable and stable. It is also an advantage to provide efficient methods for forming such compounds and structures, and intermediates useful for such purposes.

These and other advantages of the present invention will become apparent after study of the following specification and claims.

DETAILED DESCRIPTION OF THE PREFERRED EMBODIMENTS

General Overview

Figure 1:
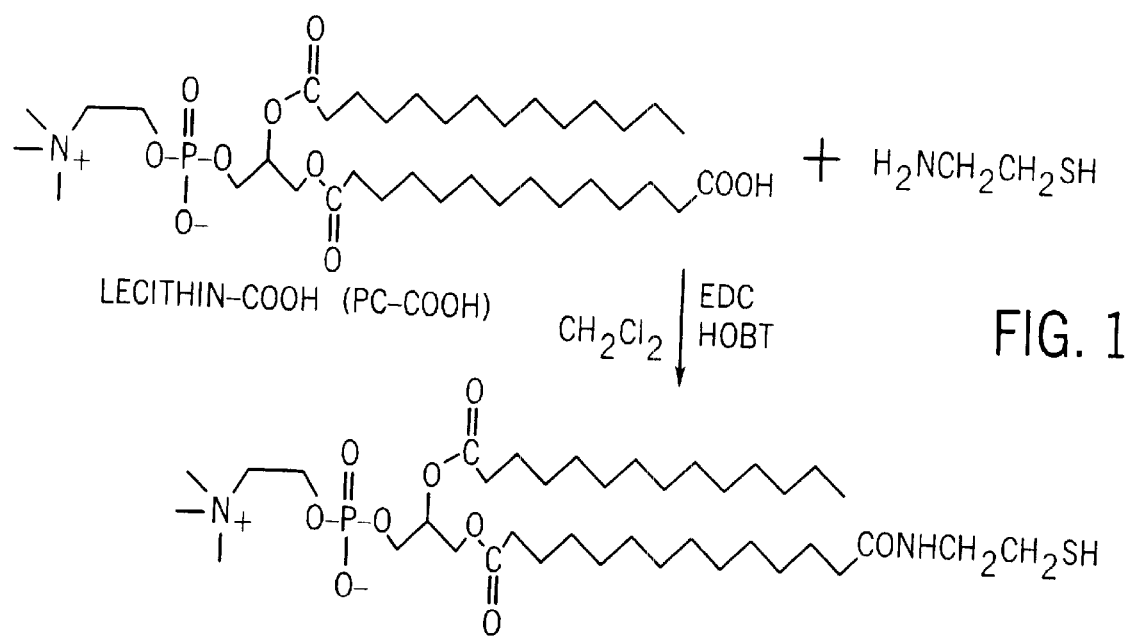
FIG. 1 is a schematic of a synthesis of thiol-linked phospholipids of the present invention.
Figure 2:
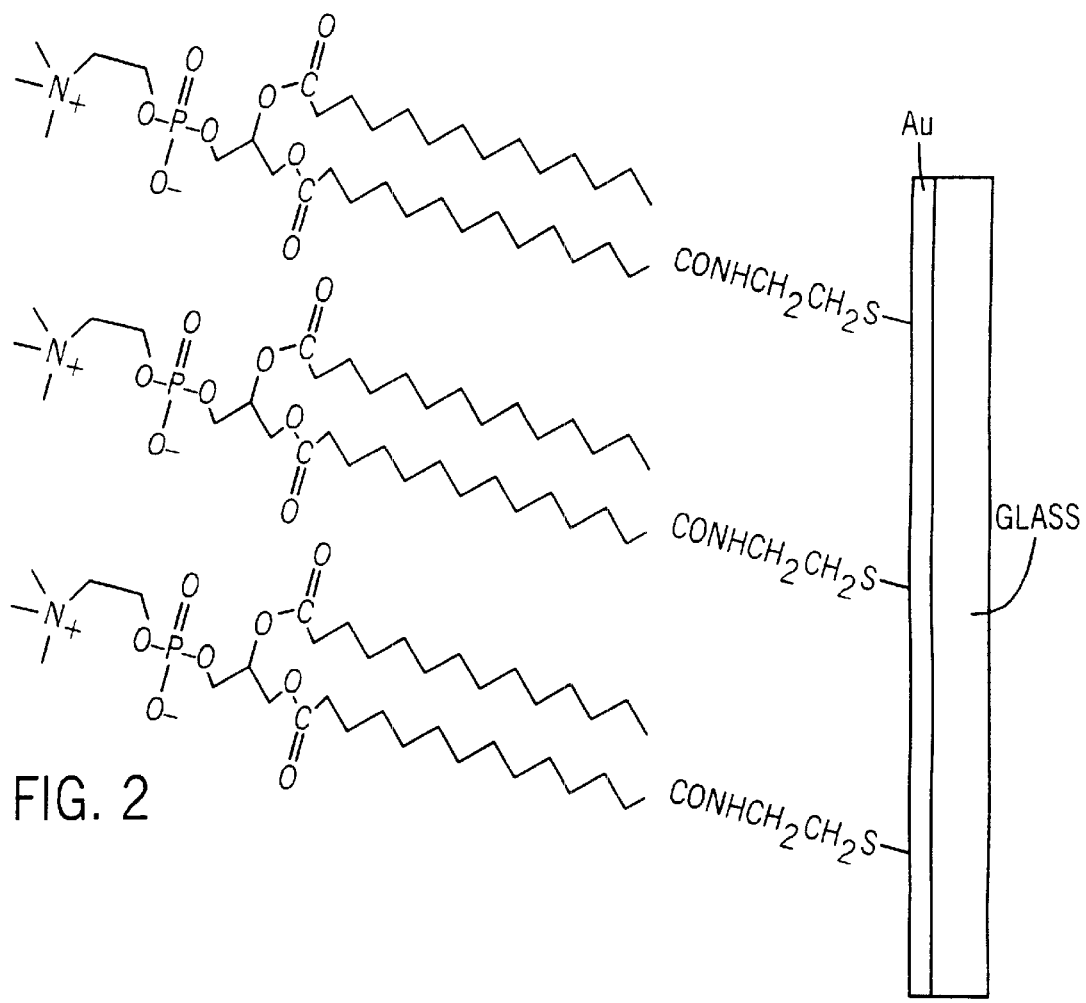
FIG. 2 depicts phospholipids arrayed in a monolayer.

For a preferred embodiment, we constructed a phospholipid monolayer on a thin gold surface. The layer is stably bound and resembles (both in terms of structure and functionality) the outer half-plane of a naturally occurring phospholipid bilayer membrane.

We synthesized thiol-terminated phospholipid from carboxylate-terminate phospholipid, and then built up a biomembrane mimetic surface on gold through chemisorption of thiol-terminated phospholipid on gold substrates. We then confirmed that this self-assembled phospholipid monolayer had close packing and good order on the gold surface.

In the naturally-occurring system proteins become embedded in a lipid bilayer which consists of two weakly coupled phospholipid monolayers. We therefore adsorbed lipase protein molecules and BSA protein molecules to these structures. The adsorbed lipase molecules retained their native conformation and dispersed uniformly on the surface.

EXPERIMENT

A. Materials

Monomyristoyl lysolecithin (lyso-PC) and 1-myristoyl-2-12-[(7-nitro-2-1,3-benzoxadiazol-4-yl)amino]dodecanoyl-sn-glycero-3-phosphoethanolamine (NBD-PE) in a $CHCl_3$ solution were purchased from Avanti Polar Lipids, Inc. (Alabaster, Ala.), and dilauroyl-phosphatidylcholine (DLPC) was purchased from Sigma.

*Pseudomonas cepacia* lipase (Amano LPL-200S) was obtained from Amano Pharmaceutical Co. (Nagoya, Japan).

Dicyclohexylcarbodiimide (DCC), 1,12-dodecanedicarboxylic acid, 4-N,N-dimethylaminopyridine (DMAP), carbonyldiimidazole (CDI), 2-aminoethanethiol hydrochloride, 1-hydroxybenzotriazole (HOBT), N,N-diisopropylethylamine (DIEA), 1-[3-(dimethylamino) propyl]3-ethylcabodiimide hydrochloride (EDC) and all anhydrous solvents were purchased from Aldrich Chemical Co.

The water used throughout the experiment was purified by a Milli-Q system from Millipore Co. with its initial resistivity better than 17 MΩ/cm.

B. Synthesis of 1-myristoyl-2-ω-carboxylmyristoyl-sn-3-qlycerophosphocholine (DMPC-COOH)

The DMPC-COOH was synthesized by following the procedure of C. Pidgeon et al., 176 Anal. Biochem. 36 (1989) with minor modifications. Briefly, 10 g (0.038 mole) of 1,12-dodecanedicarboxylic acid was dissolved in 200 mL anhydrous tetrahydrofuran (THF) in a dry 500 mL round bottom flask at 40° C., and 8.1 g (39 mmole) of DCC was dissolved in 20 mL anhydrous THF in a dry beaker.

The DCC solution was added to the reaction flask dropwise by a pipette while being purged with dry nitrogen, and a white suspension resulted. The reaction flask was then sealed under nitrogen and kept stirring at room temperature for 15 hours. Then, 500 mL of acetone was added and filtered through a sintered glass funnel. The filtrate was slightly cloudy and stored in a refrigerator overnight. The cloudy solution was filtered again and the solid product was collected and dried under vacuum ($<10^{-4}$ torr).

As a result, 3.5 g (~40% yield) of cyclic dodecanedicarboxylic anhydride was obtained. The product was checked for diacid impurities, which were found to be negligible. Next, 1.0 g of monomyristoyl lysolecithin (2.1 mmol), 1.7 g (7.0 mmol) of dodecanedicarboxylic anhydride, and 0.26 g (2.1 mmol) of DMAP were added into 60 mL of anhydrous chloroform in a flame dried flask. The reaction flask was sealed under nitrogen and kept stirring in the dark at room temperature for 48 hours. Chloroform was removed by roto-evaporation, and 20 mL of methanol was added to dissolve the lecithins.

After filtration, 300 mL of acetone was added to the methanol solution. The solution was stored in a refrigerator overnight, and the product was collected by filtration and then dried under vacuum. Finally, 1.15 g (~75% yield) of DMPB-COOH was obtained. The product was checked with $^1$H-NMR(300 Mhz, $CDCl_3$): δ5.20 (m, 1H), 4.33 (br, 2H), 4.10 (br, 2H), 3.95 (t, 2H) 3.77 (br, 2H), 3.34 (s, 9H), 2.27 (t, 6H, 1.05–1.35 (br, 42H, 0.87 (t, 3H); and mass spectroscopy showing the molecular ion M+1=709.

C. Synthesis of 1-myristoyl-2-ω-N-ethanethiolformamidomyristoyl-sn-3-glycerophosphocholine (DMPC-CONHCH$_2$CH$_2$SH)

The DMPC-CONHCH$_2$CH$_2$SH was synthesized by following the linking procedure of D. Seebach et al., 79 Helv. Chim. Acta 913 (1996) and M. Bodanszky et al., The Practice of Peptide Synthesis, 119 Springer-Verlag, Berlin (1994), with minor modification. Briefly, 400 mg (0.57 mmol) of 1-myristoyl-2-ω-carboxylmyristoyl-sn-3-glycerophosphocholine (DMPC-COOH), 0.193 g (1.70 mmol) of 2-aminoethanethiol hydrochloride, 0.076 g (0.57 mmol) of 1-hydroxybenzotriazole (HOBT) and 0.2 mL (1.16 mmol) of N,N-diisopropylethylamine (DIEA) were dissolved in 15 mL anhydrous methylene dichloride in a dry 50 mL round bottom flask, the solution is stirred and cooled in an ice-water bath while 0.139 g (0.73 mmol) of 1-[3-(dimethylamino)propyl]-3-ethylcabodiimide hydrochloride (EDC) in 5 mL was added and reaction flask was sealed under nitrogen.

Stirring is continued for 30 minutes at 0° C. and additional 48 hours at room temperature. The reaction mixture was then washed with 20 mL of 1.0 N HCl solution for three times to remove any unreacted ethanethiol and DIEA, and subsequently washed with 5% $NaHCO_3$ solution for three times. The organic phase was collected and solvent was removed by rotatory evaporation under reduced pressure at room temperature. The product was dried in a vacuum. As a result, 150 mg of DMPC-CONHCH$_2$CH$_2$SH was obtained. The product was checked with $^1$H-NMR (300 Mhz, $CD_3Cl/CD_3OD$) δ5.20 (m, 1H), 4.33 (br. 2H), 4.10 (br. 2H), 3.95 (t, 2H), 3.77 (br. 2H), 3.5–3.4 (m, 2H), 3.34 (s, 9H), 2.66 (t, 2H), 2.27 (t, 6H), 1.05–1.35 (br. 42H), 0.87 (t, 3H);

D. Preparation of Gold Substrate

The gold was deposited in a film layer by sputtering it on the glass slide surface in a thermal metal evaporation device at vacuum of $2 \times 10^{-6}$ torr. The rate of gold evaporation and the film thickness were controlled by a quartz resonance sensor. The condition of gold film preparation were evaporation rate 10 Å/s and annealing time 60 minutes to give a gold film thickness of 470 Å.

E. Preparation of the Phospholipid Linked Surface

The gold substrate was immersed in a 1 mM solution of DMPC-CONHCH$_2$CH$_2$SH in mixed solvent of methylene chloride and methanol (2:2 v/v) for 24 hours. The resulting substrate was then taken out, washed with mixed solvent of methylene chloride and methanol (2:1 v/v) and dried by nitrogen.

F. Bindinq Tests

In our experiment we used a BSA solution (ca. 250 mg/L) in citrate phosphate buffer of phospholipid 7.8 and ionic strength of 0.107M for 1 hours, and then rinsed with water for 1–2 minutes.

For lipase adsorption, crude lipoprotein lipase LPL 200S, which is mixture of glycine and lipase, from *Pseudomonas cepacia* was first purified by a Sephadex G-25 fine gel column. See K. Tanaka et al., Langmuir (1999). The percent yield for this purification process was typically 40–50%. This is in agreement with the fact that the unpurified lipase mixture contains approximately 50% glycine by weight. Then, the substrate was soaked in the lipase solution with the concentration of 337/mg/L. After soaking for 4 hours, the substrate was taken out and rinsed in the water for 5 minutes.

G. Analysis of Bound Protein

Polarization modulation Fourier transform infrared reflection-adsorption (PM-FT-IRRAS) spectra of 1000 scans at 2 cm-1 resolution were obtained with a Mattson RS-1 spectrometer and a narrow-band HgCdTe detector.

The thickness of phospholipid monolayer on gold substrate and absorbed protein were determined with the optical technique of surface plasmon resonance. The surface morphology was analyzed by atomic force microscopy.

H. Results and Discussion

Molecules of thiol-terminated phospholipid were chemisorbed onto a fresh polycrystalline gold surface by immersion for approximately 24 hours in a 1 mM solution in mixed methylene and methanol with the ratio of two to one. Immersion of gold substrate for a longer period such as 3 and 4 days, no spectroscopic differences were observed.

In order to confirm that the phospholipid were indeed chemisorbed on gold surface via the reaction between gold and thiol group of phospholipid, spectroscopy was employed as primary method for monitoring the chemical structure of adsorbed monolayer. After thoroughly rinsing with mixed solvent of methylene and methanol, the measurement was made. We confirmed that the aminoethanthiol molecule had attached to the end of acyl chain of DMPC by the amide linkage. We also observed peaks indicating that the thio-terminated DMPC had already adsorbed on the gold surface.

Other tests indicated that the thiol-terminated phospholipid was coated on gold surface by chemisorption in a manner which was highly ordered and closely-packed. Still other tests indicated that a conformal monolayer surface is present on gold surface.

To investigate the interaction between blood protein and lipid SAM on gold surface, an adsorption experiment of BSA on phospholipid monolayer was carried out. The thickness of adsorption layer was measured by surface plasmon resonance. The absorbed BSA thickness on thiol-terminated phospholipid monolayer is only 7 Å. This result suggests that the conformation of BSA molecules is not much perturbed by the lipid monolayer since the phospholipid monolayer provides a native environment similar to the biomembrane. The adsorption of BSA on lipid monolayer was significantly depressed and almost no BSA adsorption occur on such monolayer by comparison with the dimension of BSA molecules.

*Pseudomonas Sp.* lipase, a water soluble extrinsic protein was chosen as an study candidate. Lipases in general trend to adsorb into the lipid/water interfaces.

The above disclosure is merely of the preferred embodiments. For example, the alkyl sections of the phospholipids can be of different sizes. Further, the substrate to which the phospholipid is linked may be gold/silver mixtures, silver, or a ceramic-containing silicon such as silicon dioxide.

Also, while the preferred substrate is gold that has been sputtered onto a base glass surface, other ways of forming the base layer are possible as well. Thus, the invention is not to be limited to just the preferred embodiments disclosed above. Rather, the claims should be looked to judge the full scope of the invention.

INDUSTRIAL APPLICABILITY

The present invention provides biomimetic surfaces useful in the formation of medical device surfaces.

We claim:

1. A compound having the following moiety:

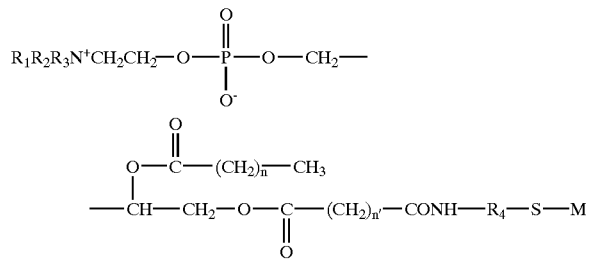

wherein each of $R_1$, $R_2$ and $R_3$ are individually selected from the group consisting of $CH_3$ and H;

wherein $R_4$ is alkyl with less than six carbon;

wherein n is 10 to 24;

wherein n' is 10 to 24; and wherein M is selected from the group consisting of Au, Ag and mixtures thereof.

2. The compound of claim 1, wherein both n and n' are 12.

3. The compound of claim 1, wherein M is Au.

4. The compound of claim 1, wherein each of $R_1$, $R_2$ and $R_3$ are $CH_3$, and $R_4$ is $CH_2CH_2$.

5. A compound having the following formula:

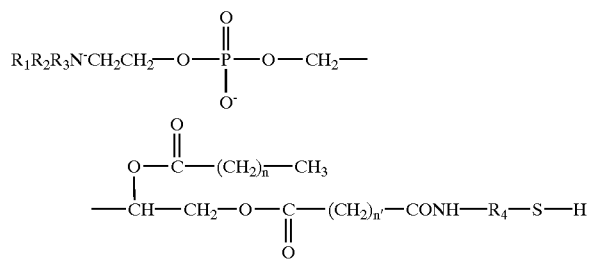

wherein the group consisting of $CH_3$ and H;

wherein $R_4$ is alkyl with less than six carbon;

wherein n is 10 to 24; and wherein n' is 10 to 24.

6. The compound of claim 5, wherein both n and n' are 12.

7. The compound of claim 5, wherein each of $R_1$, $R_2$ and $R_3$ are $CH_3$, and wherein $R_4$ is $CH_2CH_2$.

8. A method of forming a compound of claim 1 comprising:

reacting a compound having the following moiety:

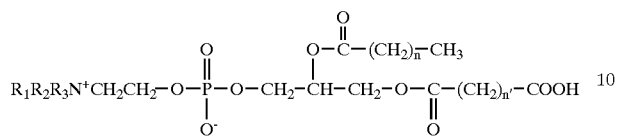

with $H_2N—R_4—SH$, and then covalently linking the resultant to M;

wherein each of $R_1$, $R_2$ and $R_3$ are individually selected from the group consisting of $CH_3$ and H;

wherein $R_4$ is alkyl with less than six carbon;

wherein n is 10 to 24;

wherein n' is 10 to 24; and wherein M is selected from the group consisting of Au, Ag and mixtures thereof.

* * * * *